(12) United States Patent
Woellenstein et al.

(10) Patent No.: US 8,874,196 B2
(45) Date of Patent: *Oct. 28, 2014

(54) METHODOLOGY FOR AUTOMATED SIGNAL MORPHOLOGY ANALYSIS IN IMPLANTABLE ELECTROTHERAPY AND DIAGNOSTIC SYSTEMS

(75) Inventors: Matthias Daniel Woellenstein, Overijse (BE); Howard Simms, Shoreview, MN (US); Scott Mazar, Woodbury, MN (US); Robert Sweeney, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 708 days.

This patent is subject to a terminal disclaimer.

(21) Appl. No.: 12/716,521

(22) Filed: Mar. 3, 2010

(65) Prior Publication Data

US 2010/0160806 A1 Jun. 24, 2010

Related U.S. Application Data

(62) Division of application No. 11/381,663, filed on May 4, 2006, now Pat. No. 7,702,383.

(51) Int. Cl.
*A61B 5/04* (2006.01)
*A61B 5/0452* (2006.01)

(52) U.S. Cl.
CPC .................... *A61B 5/0452* (2013.01)
USPC ........................................................ 600/509

(58) Field of Classification Search
CPC ..................................................... A61B 5/0452
USPC ......................................................... 600/509
See application file for complete search history.

(56) References Cited

U.S. PATENT DOCUMENTS 5,431,691 A 7/1995 Snell et al.
5,954,666 A * 9/1999 Snell .............................. 600/523

(Continued)

OTHER PUBLICATIONS

"U.S. Appl. No. 11/381,663, Restriction Requirement mailed Feb. 25, 2009", 9 pgs.

(Continued)

*Primary Examiner* — Christopher D Koharski
*Assistant Examiner* — Jeremiah Kimball
(74) *Attorney, Agent, or Firm* — Schwegman Lundberg & Woessner, P.A.

(57) ABSTRACT

Systems and related methods for analyzing data sensed from a device implanted in a patient, such as a cardiac pacing system. The system detects and evaluates electric signals within the patient that share a common event marker. By using algorithms and graphical presentation of the collected signals having common event markers, deviations in signals over time can be identified and evaluated in consideration of taking further action related to the patient and the implanted device. The system can also be used in conjunction with an advanced patient management system that includes a programmer or repeater capable of gathering information from the implanted device and transmitting the data to a host via a communications network for evaluation at a remote location.

20 Claims, 9 Drawing Sheets

(56) References Cited

U.S. PATENT DOCUMENTS

| | | | |
|---|---|---|---|
| 5,974,341 | A | 10/1999 | Er et al. |
| 6,016,442 | A | 1/2000 | Hsu et al. |
| 6,324,423 | B1 | 11/2001 | Callahan et al. |
| 6,415,175 | B1 | 7/2002 | Conley et al. |
| 6,418,340 | B1 | 7/2002 | Conley et al. |
| 6,449,504 | B1 | 9/2002 | Conley et al. |
| 6,522,925 | B1 * | 2/2003 | Gilkerson et al. ............. 607/30 |
| 6,564,091 | B2 | 5/2003 | Shekhar |
| 6,577,894 | B2 | 6/2003 | Callahan et al. |
| 6,665,558 | B2 | 12/2003 | Kalgren et al. |
| 7,299,086 | B2 * | 11/2007 | McCabe et al. ............. 600/509 |
| 2004/0127958 | A1 | 7/2004 | Mazar et al. |
| 2006/0167520 | A1 * | 7/2006 | Gilkerson et al. ............. 607/30 |
| 2006/0265020 | A1 * | 11/2006 | Fischell et al. ................. 607/30 |
| 2007/0260149 | A1 | 11/2007 | Woellenstein et al. |

OTHER PUBLICATIONS

"U.S. Appl. No. 11/381,663 Restriction Requirement mailed May 6, 2009", 6 pgs.

"U.S. Appl. No. 11/381,663, Notice of Allowance mailed Jul. 27, 2009", 7 Pgs.

"U.S. Appl. No. 11/381,663, Notice of Allowance mailed Nov. 18, 2009", 5 Pgs.

"U.S. Appl. No. 11/381,663, Preliminary Amendment filed Oct. 27, 2009", 5 pgs.

"U.S. Appl. No. 11/381,663, Response filed Mar. 26, 2009 to Restriction Requirement mailed Feb. 25, 2009", 6 pgs.

"U.S. Appl. No. 11/381,663, Response filed Jun. 8, 2009 to Restriction Requirement mailed May 6, 2009", 6 pgs.

* cited by examiner

| Event Marker | Common Events | Uncommon Events |
|---|---|---|
| Atrial Sense (AS) | | |
| Atrial Pace (AP) | | |
| Right Ventricle Sense (RVS) | | |
| Right Ventricle Pace (RVP) | | |
| Left Ventricle Sense (LVS) | | |
| Left Ventricle Pace (LVP) | | |

FIG. 9

METHODOLOGY FOR AUTOMATED SIGNAL MORPHOLOGY ANALYSIS IN IMPLANTABLE ELECTROTHERAPY AND DIAGNOSTIC SYSTEMS

CROSS REFERENCE TO RELATED APPLICATION

This application is a divisional of U.S. application Ser. No. 11/381,663, filed May 4, 2006, now issued as U.S. Pat. No. 7,702,383, which is hereby incorporated by reference in its entirety.

TECHNICAL FIELD

The present method relates generally to implantable medical devices and more particularly relates to systems and methods for analyzing electrical signals present in a patient based on event classification of the signals.

BACKGROUND

Management of patients with chronic disease poses many challenges. Chronic diseases such as heart failure, asthma, COPD, chronic pain, and epilepsy, are event driven. Some example implantable devices for use in heart disease treatment include pacemakers, implantable cardioverter defibrillators (ICDs), and heart failure cardiac resynchronization therapy (CRT) devices. Often, implanted devices are used to monitor a patient's condition before, during, and after treatments applied by the implanted device. Implanted devices are often designed to monitor conditions and performance of the device itself.

The implantable devices can be configured to separately monitor or sense the electro-physiologic data associated with different organs or types of tissue in a patient (e.g., neurological tissue, cardiac muscle, and skeletal muscle). This data, when appropriately analyzed, can provide the clinician with a valuable diagnostic and/or prognostic tool to more accurately assess a status of patient health or the diagnostic state of the implantable device.

SUMMARY OF THE INVENTION

The present invention generally relates to systems and methods for analyzing data sensed from a device implanted in a patient, such as a cardiac pacing system. The system detects and evaluates electric signals within the patient that share a common event marker. Using algorithms, charts, and graphical presentation of the collected signals having common event markers, deviations in signals over time can be identified and evaluated in consideration of taking further action related to the patient or the implanted device. The system can also be used in conjunction with an advanced patient management system that includes a programmer or repeater capable of gathering information from the implanted device and transmitting the data to a host via a communications network for evaluation at a remote location.

The various embodiments described above are provided by way of illustration only and should not be construed to limit the invention. Those skilled in the art will readily recognize various modifications and changes that can be made to the present invention without following the example embodiments and applications illustrated and described herein, and without departing from the true spirit and scope of the present invention, which is set forth in the following claims.

BRIEF DESCRIPTION OF THE DRAWINGS

The invention can be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE PREFERRED EMBODIMENT

The systems and methods described herein can be used to analyze electrical signals in a patient, such as neurological and cardiovascular waveforms. The electrical signals can be generated from a signal source such as, for example, a mechanical sensor, a chemical sensor, or the intrinsic electrical activity generated by a patient's body. The example systems and methods disclosed herein provide for the use of an implanted device, collection of a signal present in the patient, whether a signal is an intrinsic event sensed by the device or a therapeutic signal generated by the device, analysis of the collected signal, and a decision concerning what the signal means. The example systems and methods can also include presentation of the analyzed collected signal to a physician for visual inspection.

The state and action of the device is referred to as an event marker. Event markers can be identified in part by aspects of the collected signal. Identification of event markers can also be identified in part by the known activity of the implantable device.

In one example application, the electrical signals analyzed include cardiovascular data sensed from a cardiac rhythm management ("CRM") device. This application provides detection and evaluation of changes in a cardiac pacing system using a methodology of combined event marker and intra-cardiac signal analysis. Telemetric pulse generator ("PG") event markers can be used for identifying the morphologies and sequences of signal components. While the present disclosure emphasizes cardiac applications, general principles disclosed herein can also be used for analysis and evaluation of neurological waveforms and waveforms related to skeletal muscle.

I. Signal Morphology Analysis

Figure 1:
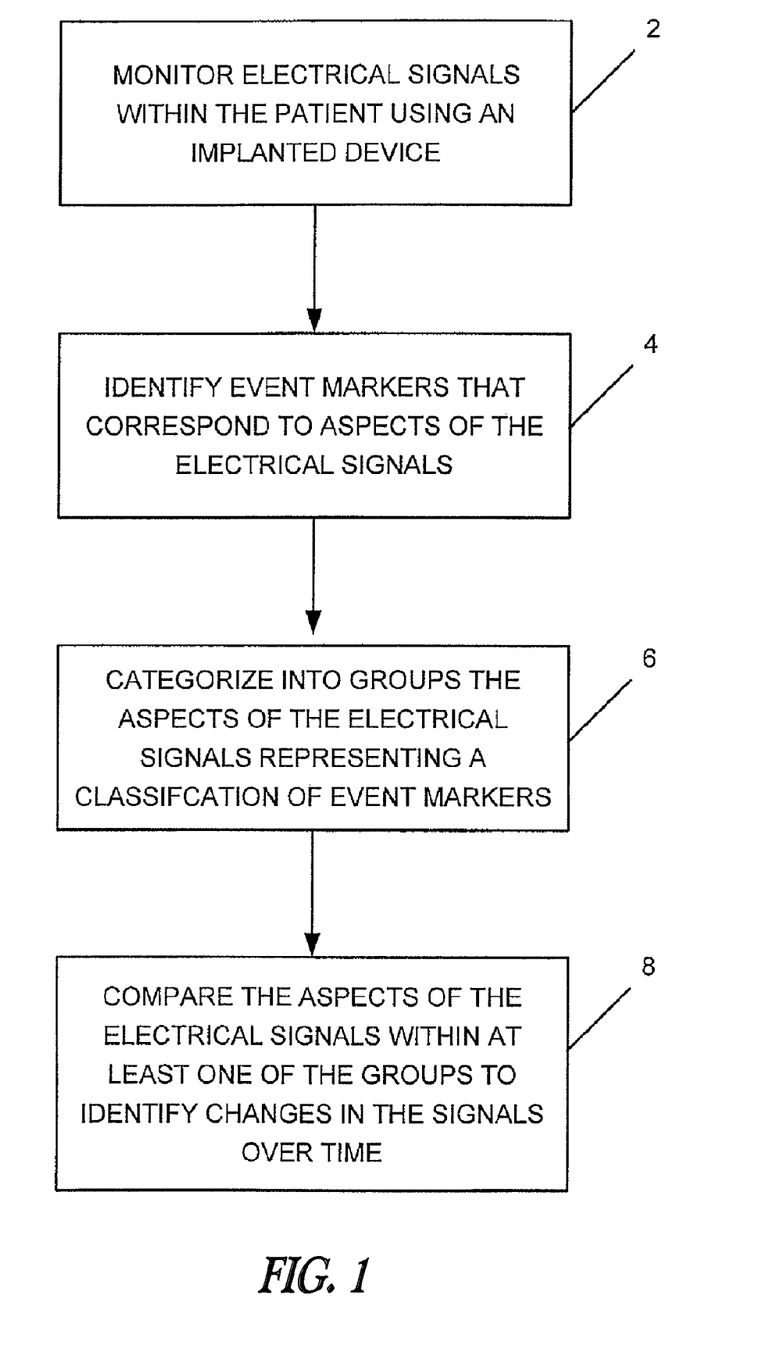
FIG. 1 is a schematic diagram illustrating an example method for analyzing signal morphology in accordance with the present invention.

Referring to FIG. 1, an example method of analyzing electrical activity in a patient is described. The method includes a step 2 of monitoring electrical signals within the patient using an implanted device, and a step 4 of identifying event markers that correspond to aspects of the electrical signals. The method of FIG. 1 also includes a step 6 of categorizing into groups or bins the aspects of the electrical signals representing a type or classification of event markers, and a step 8 of comparing the aspects of the electrical signals within at least one of the groups to identify changes over time.

The method of FIG. 1 can also include other steps such as, for example, reporting the comparison for analysis by a physician, wherein the changes over time include occurrences outside of a predetermined range of electrical signal values. The method can also include analyzing identified changes over time to determine a recommended action. The step 2 of monitoring the electrical signals can include monitoring intra-cardiac electrograms generated by an implanted cardiac rhythm management device. Aspects of the electrical signal can include waveform data, wherein the waveform data in conjunction with the event markers, can be used to identify threshold deviations in the waveform data over time.

The event markers of step 4 can be used to help define boundaries of periods of the electrical signal. Those portions of the signal defined by the event markers are separated into separate groups or bins for each type of event marker. The periods of the signal can be any desired time that captures at least a portion of the signal representative of what has occurred due to the event marker. For example, the period may be about 100 to about 2000 milliseconds, and more preferably about 200 to about 1000 milliseconds. In some configurations, the time period is one heart beat, one muscle contraction, or one nerve signal or stimulus. The system can be designed to capture the period of the signal for each event marker and place that period of the signal in the bin designated for that given event marker. In some embodiments, the periods are captured a certain number of times within a given time frame (e.g., one time per hour), or are captured after a certain number of occurrences (e.g., one capture for every four occurrences of the period for a given type of event marker).

Figure 2:
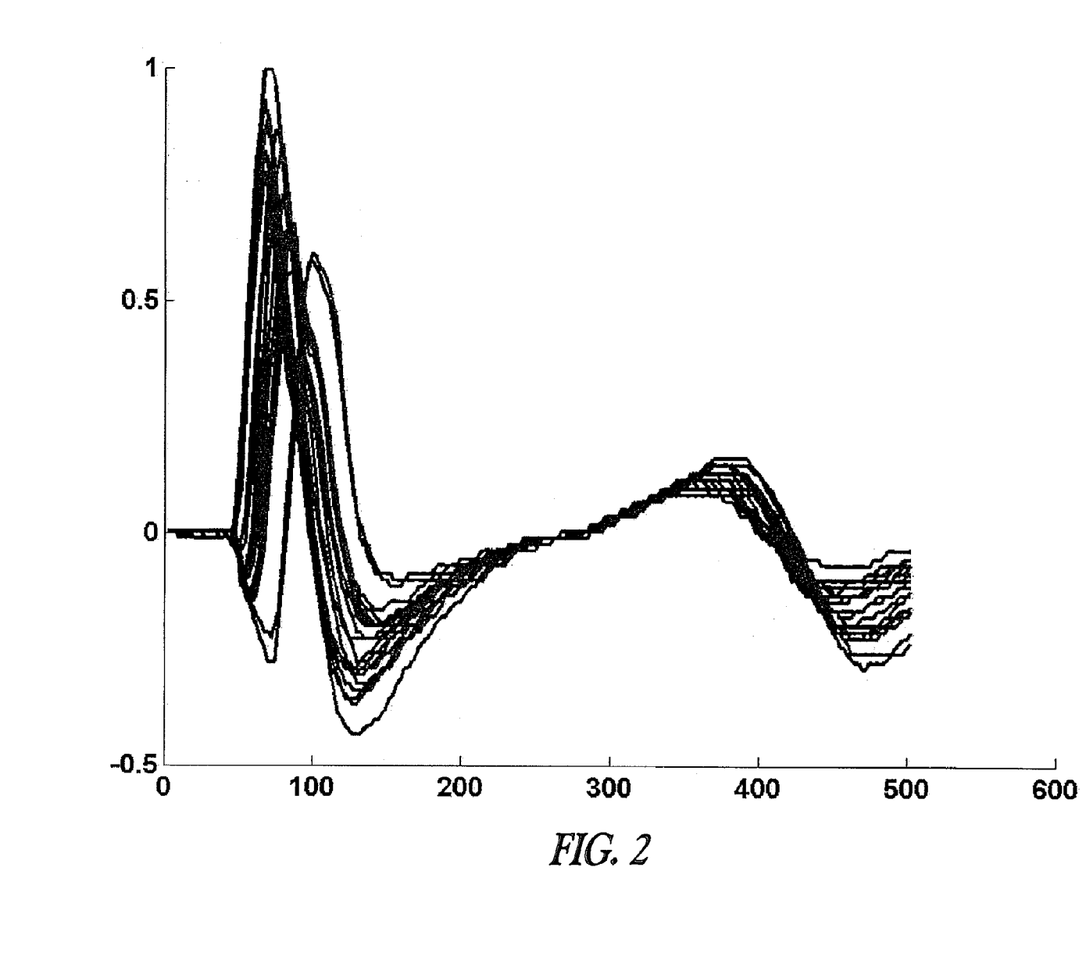
FIG. 2 is a graph illustrating an example presentation of signal information for a group of like event markers.

When using device in the patient for an extended time period (e.g., several hours, days, weeks, or years), a number of captures of periods of the signal for a given event marker are binned and available for analysis. The system executing steps of the example method described above analyzes the binned periods of the signals. Analysis of the binned periods can be handled in a variety of ways. In one example, the analysis is communicated in the form of a graph whereon the periods of the signals are plotted on top of each other, such as illustrated in FIG. 2. The graph illustrates trends over time and abnormalities. The information presented on the graph can be evaluated automatically by an electronic device such as implanted device from which the event markers are determined, a device outside of but located near the patient, or a device located remote from the patient. The analysis of binned periods can also be evaluated by such devices when the information is in other formats than in a graph. Automated evaluation by an electronic device typically involves execution of an algorithm (not shown) using a processor or other analysis device. Such algorithms can be part of a computer program.

The graft can also be presented to and viewed by the patient, the patient's physician, or a third party for further analysis. The graphed information can be presented in different colors, with different styles of lines, or other characteristics that help distinguish between, for example, subcategories of the binned periods or abnormal values. In another embodiment, the analysis information can be presented in a chart format (e.g., see FIG. 6) or other formats best suited for a given application. Review of the presented information can be used to determine whether further action (e.g., treatment, testing, repair) is needed.

Analysis of the binned information can be centered around monitoring of consistent performance of the periods of the signal within a bin. Departures outside of the consistent performance (e.g., outside of a predetermined range of values) can indicate a problem or the potential of a problem occurring, for example, with the patient's health (e.g., improper response to treatments) or the implanted device. Analysis of the binned periods can also provide information about how often inconsistent performance occurs.

The binned periods of signals can be averaged over different time periods and that information evaluated. For example, the periods of signal captured in a bin during a set time interval (e.g., a day, a week, or a month) can be averaged for that time interval and then compared to the average values from previous and future occurrences of that time interval.

The bins or groups related to different event markers can be further or additionally categorized based on other physical indicia such as, for example, heart rate and blood pressure.

While the above description uses an implanted device as an important part of carrying out functions of the system, other devices can provide similar results. For example, devices secured to an outer surface of the patient (e.g., a surface echocardiogram) can be used to generate signals, sense electrical signal, and provide a basis for identifying event markers.

II. Example Systems and Methods for Automated Intra-Cardiac Signal Morphology Analysis Another example system 10 is shown and described with reference to FIGS. 3-7. The system 10 is directed to a system for automated intra-cardiac signal morphology analysis.

When a telemetric pulse generator (PG) or other implanted device delivers therapy (e.g., in the form of electronic stimuli or shocks), the PG can be adapted to record or mark the delivered therapy event in a memory component of the device. The PG can further be adapted to record the sensing events of a lead of the PG that is couple to the patient (e.g., to the patient's heart). This allows a clinician to interrogate the device's memory to obtain a historical view of the patient's health status and any therapy delivered by the PG.

Cardiac rhythm management ("CRM") devices can be used with an external device such as a programmer or controller that communicates with the CRM. Programmers are typically adapted to electronically communicate with a CRM by sending data to and receiving data from the device. Physicians or other medical personnel use such controllers to monitor and control the functions of the implanted device typically during in-person visits by the patient to a clinic.

An external device can also be configured to interrogate a CRM or PG/Lead system. In such a configuration, the device is often referred to as a communicator or repeater. The monitoring or interrogation mode of an external programmer or repeater is primarily used as a diagnostic tool to evaluate the implanted device and patient between office visits. However, CRM interrogation typically does not involve any temporal correlation and/or analysis of an operational event of the CRM with a physiologic response or event sensed by the CRM. With the use of device and/or sensed event markers as points of reference, the clinician has a temporal record of data that can be correlated and analyzed to detect any changes or anomalies with the device or with the expected therapeutic results. A temporal correlation can not only provide the clinician with valuable information on the operation of the CRM and its leads, but also provide the clinician with equally valuable information on the clinical status of the patient.

When such an external device is connected to a remote server or database, the information can be made available to any clinician. Thus, a clinician or specialist in a remote location can monitor and evaluate the PG/Lead system and the patient and potentially reduce the frequency of in-office assessments or, conversely, quickly identify the need for a personal assessment based on analysis of the information transmitted to the server or database.

The example systems and method described herein are configured to evaluate an implanted PG/Lead system based on a PG event marker and/or intra-cardiac electrograms ("EGMs") that allow a clinician to distinguish between changing signal morphologies in an implanted system that represent, for example, a device malfunction, an unexpected signal source, or a change in the clinical state of a patient. The example systems and methods allow a clinician in a remote setting to determine the frequency of, or urgent need for, an in-office evaluation based upon the analysis of marked events. In these ways, the systems and methods disclosed herein can assist in lowering the cost of medical care by providing remote oversight of the operation and therapy provided by the PG/Lead system and increasing awareness of physiologic system influences.

One example system uses a plurality of intra-cardiac event markers including, but not limited to, Atrial Sense ("AS"), Atrial Pace ("AP"), Left Ventricular Sense ("LVS"), Left Ventricular Pace ("LVP"), Right Ventricular Sense ("RVS"), and Right Ventricular Pace ("RVP") markers. These lead specific PG markers can then be analyzed to identify common or uncommon events associated with a specific event marker. By way of non-limiting example only, the AS marker can be graphically displayed over a period of time representing a series of AS events that allow the clinician to quickly and visually observe any deviations.

The EGMs can be organized in bins for different event markers. The EGMs can be represented by predefined time intervals such as, for example, a single beat of the heart rate at the time the EGM was recorded. Binning permits separation of paced events at different rate thresholds. For example, a waveform of paced events can be analyzed and compared in view of a maximum tracking rate ("MTR") versus paced events at a lower rate limit ("LRL"). MTR and LRL can be considered the extremes of normal behavior for a dual chamber pace maker. In one embodiment, the system provides separation of paces and senses that occurred during altered pacing support states, such as post-shock pacing, atrial tachycardia response mode switching, etc. In this way the system provides drawing of EGMs within a bin over each other, so that the clinician can observe the frequency at which different waveforms are detected. More frequent waveforms are drawn in a "hotter" color (e.g., red), which would give the clinician a sense of not only what waveforms are occurring, but also how often those waveforms are occurring for the patient.

In a further example system, the same signal and marker information can be correlated against expected values to identify deviations in signal morphology. For example, an expected AS event can be translated into an algorithmic expression that can include an acceptable range of deviation. If an AS event occurs outside the acceptable range, that event can be flagged or identified for further evaluation and analysis by a clinician. Patients without events demonstrating intra-cardiac signals significantly different in morphology can be eligible to a reduced frequency of in-office evaluation. Conversely, events presenting themselves outside the expected range for signal morphology variations can prompt an increased frequency of in-office evaluation.

Example systems and methods disclosed herein operate from a premise that typical signal morphologies of events in an EGM are relatively stable. Any change in morphology is associated with a specific root cause or condition. Conditions that can have an influence on signal morphologies, amongst others are:

Oversensing
Undersensing
Loss of Capture
Dislocation
Lead Fracture
Body Posture
Time of day
Patient Salt Intake
Medication
Exercise A device associated with the afore-mentioned example systems and methods can include an external device such as, for example, a programmer or repeater that is compatible with a PG/Lead system. Such an external device is typically used to monitor and control the operation of the PG/Lead system. In addition, the programmer or repeater can be configured to interrogate and record the event markers recognized by the PG/Lead system. The programmer or repeater is capable of storing an amount of data that typically far exceeds the capabilities of the PG/Lead system. This stored data can be made accessible to a clinician who analyzes and evaluates historical patient data, including comparing patient data collected from different patients. The clinician analysis can be done remotely as well as during in-clinic patient visits.

The programmer or repeater can be a component of an advanced patient management ("APM") system or network adapted to store and analyze diverse patient data and information (see below for further details of an APM application). In an APM, population data can also be accessible to the clinician so that the clinician can analyze a specific patient's data within the context of a population of patients. This type of analysis can reveal or disclose the impact of environmental factors on a status of patient health.

Some example systems and methods use algorithmic and graphical presentations of sensed events and deviations therefrom. Such systems and methods can employ the use of a PG/Lead system with memory capabilities to allow capturing of sensed events over an extended time period. Some systems can also include a programmer or repeater capable of interrogating the data stored in the PG/Lead system and transmitting that data to a computer network that is part of, for example, an APM system.

The use of event markers for filtering intra-cardiac signals into main event morphologies can provide several advantages such as filter out signal sequences that are market as noise by the device, using the PG-based event marker classification by the device to identify main signal components (AS, AP, RVS, RVP, LVS, LVP), isolate signal components with a sufficient amount of signal time prior to and after the event marker, and application of a mathematical signal processing method to those components within one group to identify either significantly common or different signal morphologies. In a securely implanted and programmed PG/Lead system, one or more of the six major signal components will have a repetitive morphology, including consistent morphology of outliers indicating under- or over-sensing as well as non-capture situations when the PG/Lead system fails to sense an event marker or capture an event marker.

The use of event markers for filtering intra-cardiac signals into main event sequences can provide several advantages such as filtering out signal sequences that are market as noise by the device, using the PG based event marker classification by the device to identify main signal components (AS, AP, RVS, RVP, LVS, LVP), and isolating individual sequences of signals with a sufficient amount of signal time prior and after to the event sequence. A search within the event markers can result in identifying one or more of the following four main event sequences:

| | |
|---|---|
| Atrial Sense Event followed by Ventricular Sense Event | AS-VS |
| Atrial Pace Event followed by Ventricular Sense Event | AP-VS |
| Atrial Sense Event followed by Ventricular Pace Event | AS-VP |
| Atrial Pace Event followed by Ventricular Pace Event | AP-VP |

Another advantage includes the ability to apply a mathematical signal processing method to those signal sequences within one group to automatically identify either significantly common or different signal morphologies. Another advantage is that a clinician can observe, detect and review changes. A still further advantage is that additional subdivisions of sensing and pacing sequences can be employed depending on the needs of the patient.

In an implanted and programmed PG/Lead system, major signal/marker sequences usually have a repetitive morphology. Some example repetitive morphologies include consistent morphology of outliers indicating under- or over-sensing as well as non-capture situations when the PG/Lead system fails to sense an event marker or capture an event marker.

A patient's diet can also have an effect on signal morphologies. For example, salt intake can affect myocardial electrophysiology. Thus, a PG/Lead system configured to sense serum sodium can correlate a change in serum sodium to a sensed physiologic change or a change in therapeutic modality. In this way, the methodology can also promote heightened awareness of external influences on physiologic parameters.

Example systems and methods disclosed herein also allow for an automated evaluation/identification of such influencing factors on an implanted PG/Lead system. Extracted information can be used to optimize PG programming or other medical therapy such as, for example, pharmaceutical therapy.

Figure 3:
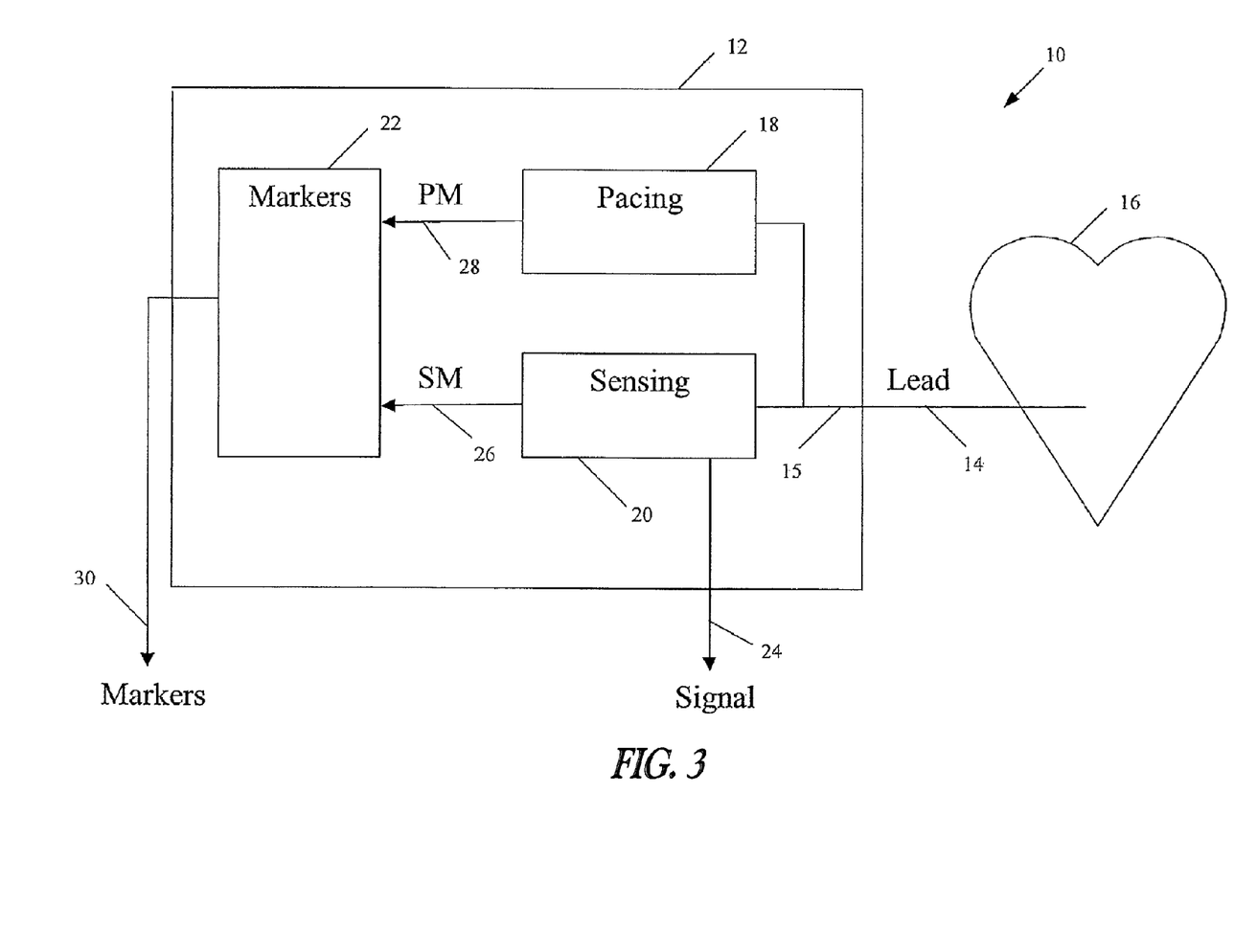
FIG. 3 is a schematic diagram illustrating an example method for automated intra-cardiac signal morphology analysis according to principles of the present invention.

The system 10 shown in FIG. 3 includes a PG 12 having a lead 14 that is coupled to a patient's heart 16. The PG includes a pacing module 18, a sensing module 20, and a marker module 22. Signals 15 transmitted via the lead 14 generally comprise intra-cardiac electrogram signals from the heart 16. The signals 15 reflect the electro-physiologic state of the patient's heart 16. These signals generally indicate, among other things, a measure of the patient's cardiac cycle, the contractility of the patient's heart chambers, and the potential presence of pulmonary obstructions such as pulmonary emboli. Signals 15, if deviant from expected norms, will typically trigger the PG 12 to emit pacing stimuli or shocks to the heart 16 to restore normal cardiac function.

The lead 14 is used to deliver pacing energy to cardiac tissue as well as sense cardiac electrical activity. Sensing using the PG 12 produces two data outputs of interest—an amplified version of measured cardiac activity 24 and sensed markers 26. Pacing produces one data output of interest—pacing markers 28. The marker module outputs the sensed markers 26 and pacing markers 28 as markers 30 from the PG 12. The markers 30 and signal output 24 are subsequently extracted, compiled and processed to create indications such as, for example, lead issues, sensing issues and physiologic changes.

Figure 4:
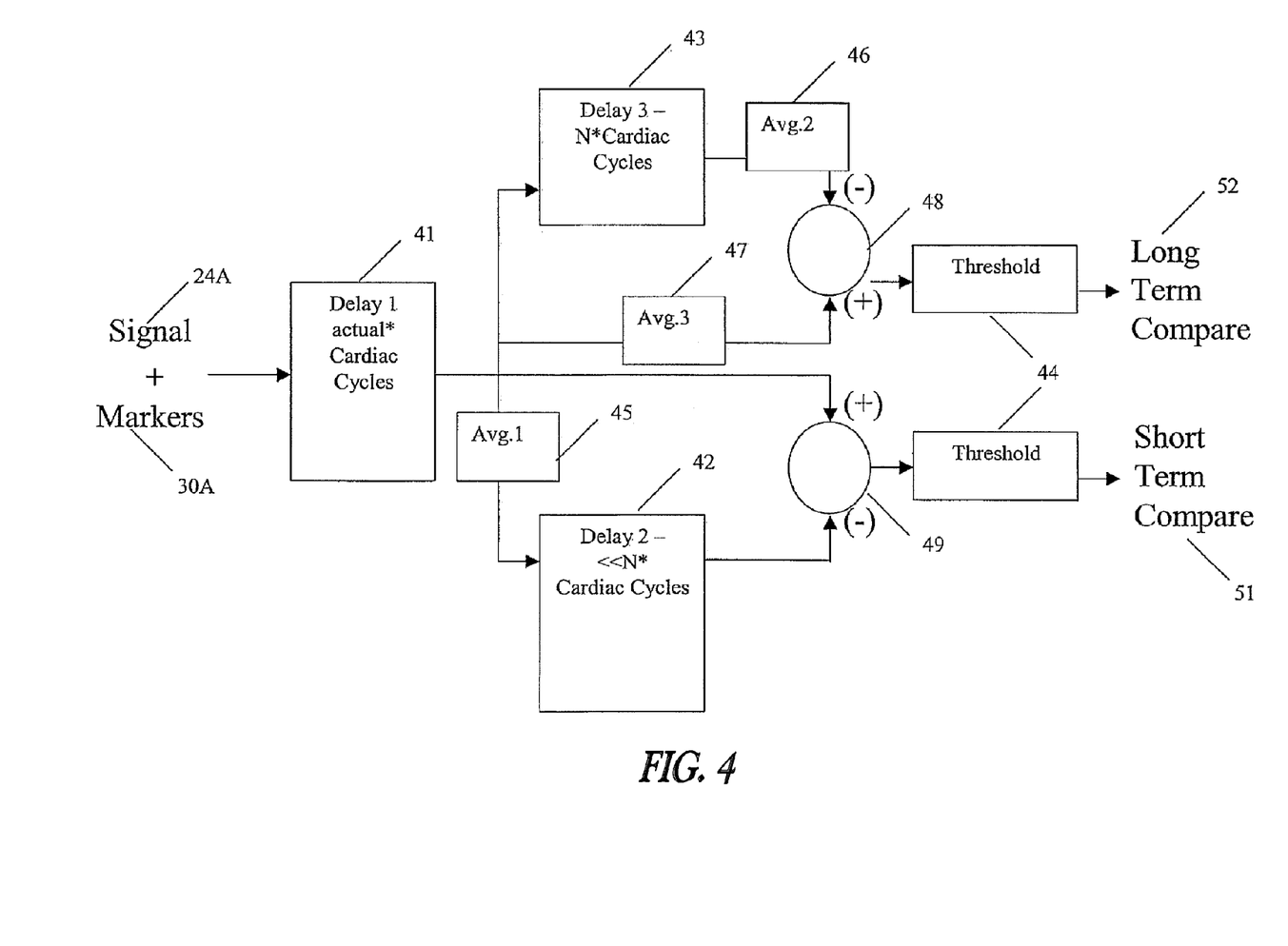
FIG. 4 is a schematic diagram illustrating another example method for automated intra-cardiac signal morphology analysis according to principle of the present invention, wherein the method includes extracting comparable signal components.

FIG. 4 illustrates aspects of another example system 40 that includes first stage signal processing for detection of short and long-term events. System 40 can be a related to system 10 shown in FIG. 3 in that the signal 24A and markers 30A used as input to the system 40 can be the outputs 24, 30 from system 10.

The functional blocks Delay 1 (41), Delay 2 (42), Delay 3 (43) and Threshold 44 can represent a single channel or multiple channel processes if there are parametric variations in operational parameters needed for selected outputs. The essential characteristic is differentiation of a single cycle comparison versus differences over multiple cycles. The threshold function is not limited to fixed threshold operations. Thresholding can incorporate fixed or adaptive operation and it can also incorporate hysteresis or other higher order linear or non-linear functions to sustain indication of onset or release of a particular event. The output of thresholds 44 are short- and long-term comparisons 51, 52 that can be used to determine particular events.

Delay functions 41, 42, 43 have dynamic lengths adjusted to match heart rate. The length of delay is controlled by periodic marker event indications with the intent of synchronizing features in the current cardiac cycle with the same features in a previous cardiac cycle. Delay 1 (41) is used to time align the beginning of a cardiac cycle with an intra-cardiac cycle feature. The Delay 1 (41) period can be seconds, minutes, days or any period that allows contextually equivalent analysis. The system 40 also includes averaging modules 45, 46, 47 and summing modules 48, 49 to assist in detecting the short- and long-term events.

Figure 5:
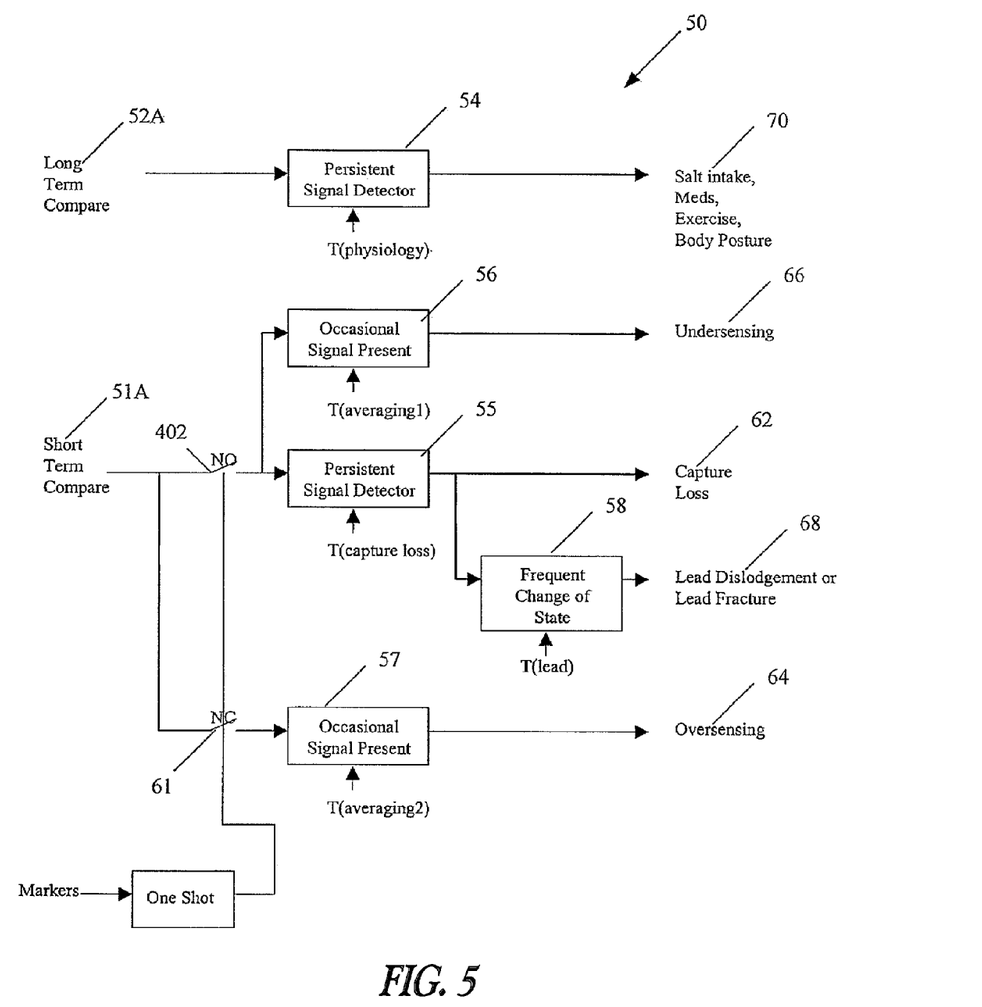
FIG. 5 is a schematic diagram illustrating a further example method for automated intra-cardiac signal morphology analysis according to principle of the present invention, wherein the method includes detecting signal deviations.

FIG. 5 illustrates aspects of another example system 50 that includes analysis of short 51A and long-term 52A comparisons that can lead to conclusions about system faults. System faults can include, but are not limited to, lead dislodgements, lead fractures, generator misprogramming, reduced output, etc. A feature of this approach is that it uses various time constants to differentiate physiological events. The Persistent Signal Detectors 54, 55 ("PSD") can, for example, be constructed from an integrator followed by a threshold. PSD output will indicate after an input persists for some T (interval) average amount of time. Occasional Signal Present detectors 56, 57 are activated when a single or small number of events occur. A Frequent Changes of State detector 58 indicates when a specified number of input state changes occur within a given time period of time.

Switches 60, 61 of system 50 indicate a gating function over which the comparison is meaningful. One example is gating the comparison function during a cardiac cycle to observe differences resulting from loss of capture 62, but sensing of electrical activity during times other than when the core cardiac cycle can indicate over-sensing 64. The system 50 includes other outputs indicating, for example, undersensing 66, lead dislodgement or fracture 68, and physical conditions 70 corresponding to, for example, salt intake, medications, exercise, and body posture.

Figure 6:
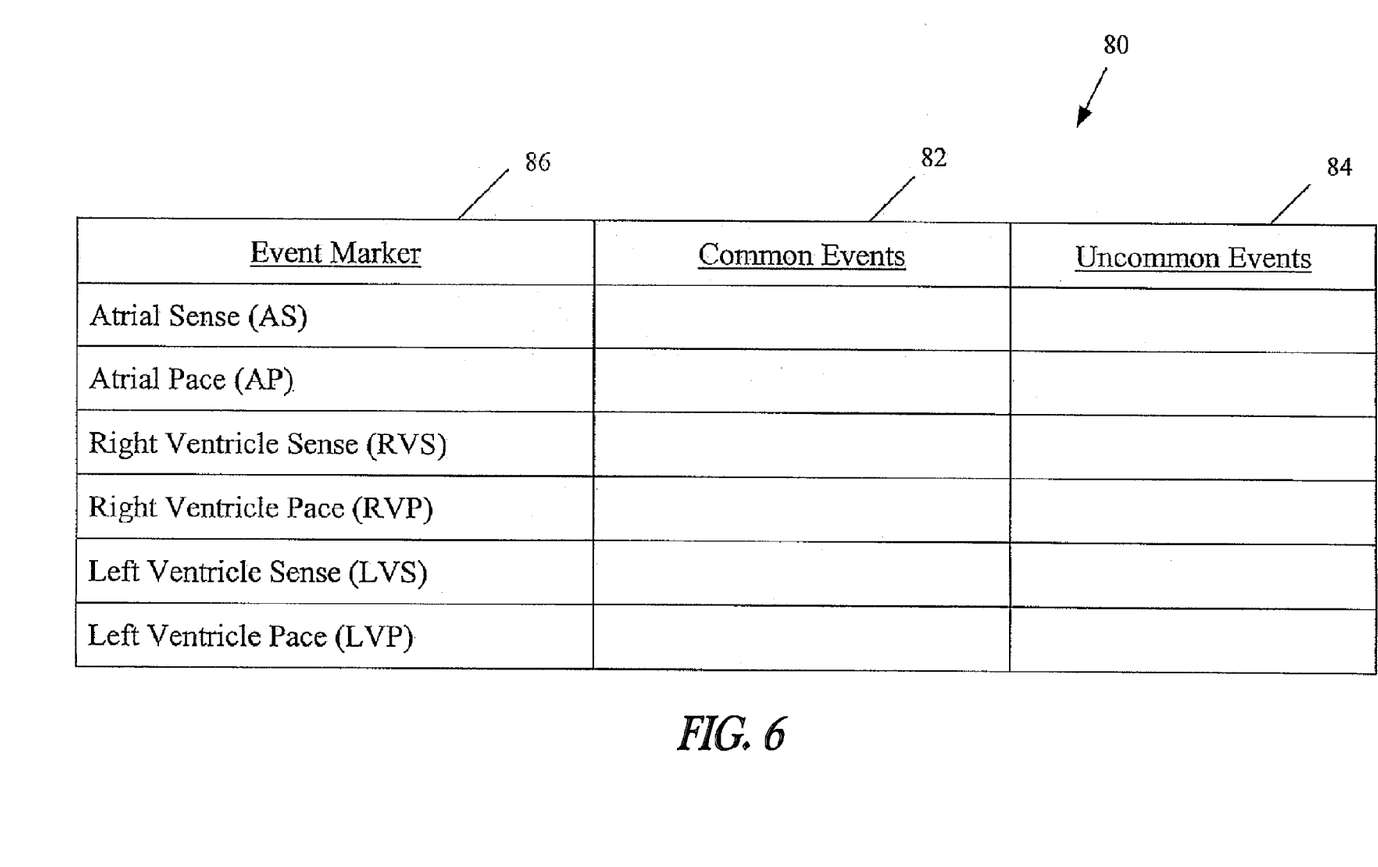
FIG. 6 is a chart illustrating intra-cardiac signal information for a group of like event markers.

FIG. 6 illustrates a chart 80 that can be used to check system integrity for systems such as, for example, systems 10, 40, 50 described above. Based on transmitted EGM signals and markers of PG events, a PG/Lead system integrity check can be performed through comparing morphologic signal criteria (not shown) and evaluating whether an individual waveform is within an expected range of variation or outside the expected range. This comparison and evaluation can provide an indication of whether the PG/Lead is functioning properly. The examination of EGM marker data can be done by visualizing whether signal waveforms (shown in FIG. 7) match corresponding PG markers in a graph format. The chart 80 can include an example "common" signal in the "common events" column 82 that can be compared visually or mathematically using algorithms to those events that are or can be considered "uncommon" (included in the "uncommon events" column 84).

FIG. 6 also provides an overview of the results of the morphologic evaluation in the form of an event-by-event or event sequence-by-event sequence visualization of event markers 86. As further shown in FIG. 6, binning or grouping waveform data according to a heart chamber to detect deviations in waveform morphology or to check system integrity can assist a clinician in evaluating a patient's unstable event morphology. This graphical aspect of the method provides an efficient process for identification of EGMs to the clinician during an in-clinic or remote device/system evaluation. While the chart 80 shows only two columns for separating signals into Common and Uncommon events, the signal can be divided into other categories gradated between extremes of common and uncommon events.

Figure 7:
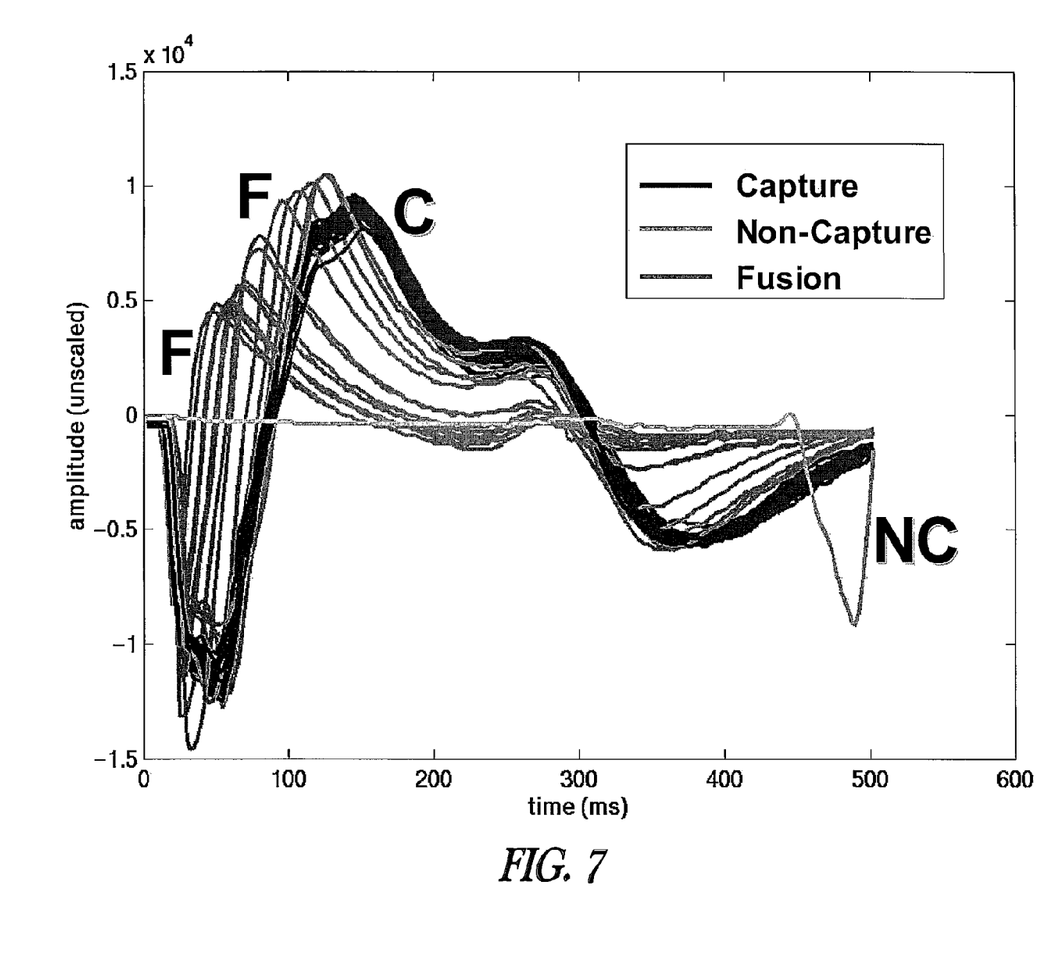
FIG. 7 is a graphic illustration of cardiac signal information for a group of like event markers that illustrates more and less frequent signal characteristics via overplotting of the signals.

FIG. 7 is a graphic illustration of cardiac signal information for a group of like event markers that illustrates more and less frequent signal characteristics via overplotting of the signals. Presentation of the signal information in this graphic format can be advantageous for purposes of obtaining a quick overview of trends and performance based on like event markers.

The example systems and methods identify changes in intra-cardiac signal morphology using algorithmic analysis. By building on the PG event classification, significantly different signal morphologies can be quickly and efficiently identified. The algorithms (not shown) and methods useful in accordance with the present disclosure can utilize the PG markers to identify typical components of the intra-cardiac signal and evaluate the PG decision process. Further, information of the physiologic process can be revealed. PG marker and system integrity data can also be analyzed using a computer network database system such as the Advanced Patient Management ("APM") system described below.

II. Advanced Patient Management System

Figure 8:
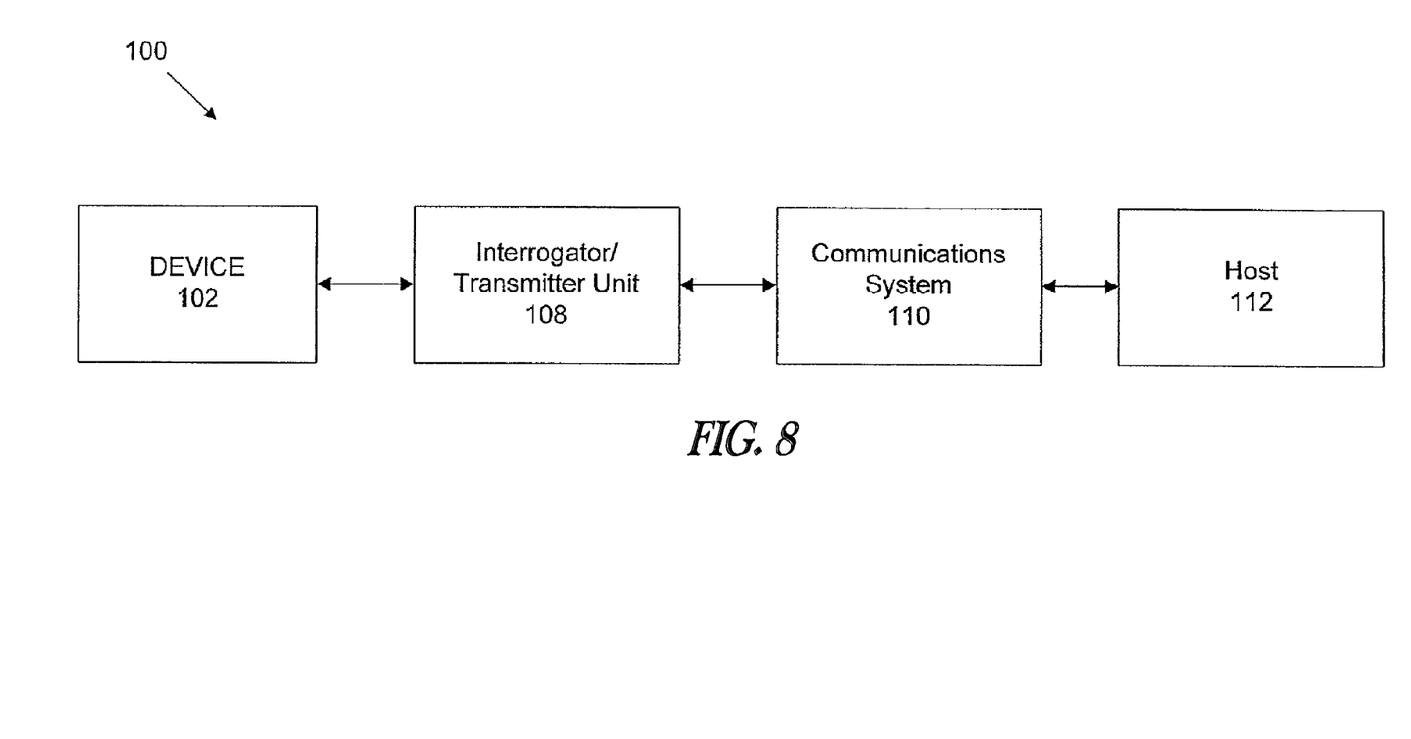
FIG. 8 illustrates schematically another example system made in accordance with the present invention.
Figure 9:
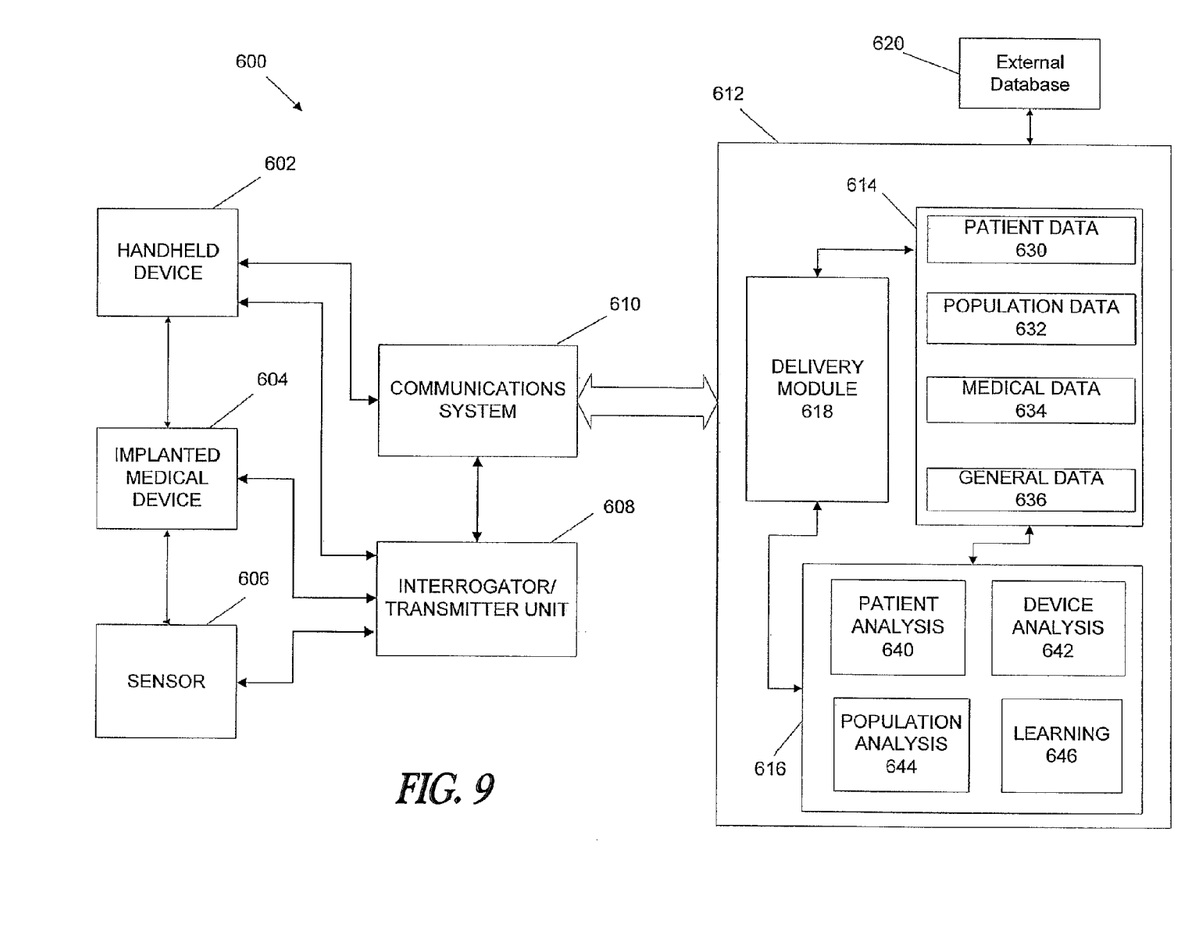
FIG. 9 illustrates an example advanced patient management system made in accordance with the present invention.

Referring now to FIGS. 8 and 9, an example system 100 for collecting and analyzing patient data is illustrated. System 100 includes a device 102, an interrogatory/transceiver unit (ITU) or repeater 108, a communications system 110, and a host 112. The system 100 can be used to, for example, communicate information to a physician or other third party for evaluation of binned signals and related event marker information. Further details related to advanced patient management systems are disclosed in U.S. Published Patent Application No. 2004/0127958, entitled ADVANCED PATIENT MANAGEMENT SYSTEM INCLUDING INTERROGATOR/TRANSCEIVER UNIT, which published application is incorporated herein by reference in its entirety.

FIG. 9 illustrates an example APM system 600 that generally includes the following components: devices 602, 604, and 606, an interrogator/transceiver unit 608, a communication system 610, and a host 612. Each component of the APM system 600 can communicate using the communication system 610. The host 612 includes a database module 614, an analysis module 616, and a delivery module 618. Host 612 preferably includes enough processing power to analyze and process large amounts of data collected from each patient, as well as to process statistics and perform analysis for large populations. For example, the host 612 can include a mainframe computer or multi-processor workstation. The host 612 can also include one or more personal computer systems containing sufficient computing power and memory. The host 612 can include storage medium (e.g., hard disks, optical data storage devices, etc.) sufficient to store the massive amount of high-resolution data that is collected from the patients and analyzed.

The database module 614 includes a patient database 630, a population database 632, a medical database 634, and a general database 636. The analysis module 616 includes a patient analysis module 640, device analysis module 642, population analysis module 644, and learning module 646.

In one embodiment, the data collected and integrated by the advanced patient system 600, as well as any analysis performed by the system 600 generally, is delivered by delivery module 618 to a caregiver's hospital computer system for access by the caregiver. A standard or custom interface facilitates communication between the APM system 600 and a legacy hospital system used by the caregiver so that the caregiver can access all relevant information using a system familiar to the caregiver.

The APM system 600 can also be configured so that various components of the system (e.g., ITU 608, communication system 610, and/or host 612) provide reporting to various individuals (e.g., patient and/or caregiver). For example, different levels of reporting can be provided by (1) the ITU 608 and (2) the host 612. The ITU 608 can be configured to conduct rudimentary analysis of data gathered from devices 602, 604, 606, and provide reporting should an acute situation be identified.

In addition to forms of reporting including visual and/or audible information, the APM system 600 can also communicate with and reconfigure one or more of the devices 602, 604, 606. For example, if device 602 is part of a cardiac rhythm management system, the host 612 can communicate with the device 602 and reconfigure the therapy provided by the cardiac rhythm management system based on the data collected from one or more of the devices 602, 604, 606. In another embodiment, the delivery module 618 can provide to the ITU 608 recorded data, an ideal range for the data, a conclusion based on the recorded data, and a recommended course of action. This information can be displayed on the ITU 608 for the patient to review or made available on the peripheral device 609 for the patient and/or clinician to review.

III. Conclusion

One or more headings have been provided above to assist in describing the various embodiments disclosed herein. The use of headings, and the resulting division of the description by the headings, should not be construed as limiting in any way. The subject matter described under one heading can be combined with subject matter described under one or more of the other headings without limitation and as desired.

The systems and methods of the present disclosure can be implemented using a system as shown in the various Figures disclosed herein including various devices and/or programmers, including implantable or external devices. Accordingly, the methods of the present disclosure can be implemented: (1) as a sequence of computer implemented steps running on the system; and (2) as interconnected modules within the system. The implementation is a matter of choice dependent on the performance requirements of the system implementing the method of the present disclosure and the components selected by or utilized by the users of the method. Accordingly, the logical operations making up the embodiments of the method of the present disclosure described herein can be referred to variously as operations, steps, or modules. It will be recognized by one of ordinary skill in the art that the operations, steps, and modules can be implemented in software, in firmware, in special purpose digital logic, analog circuits, and any combination thereof without deviating from the spirit and scope of the present invention as recited within the claims attached hereto.

The above specification, examples and data provide a complete description of the manufacture and use of the composition of the invention. Since many embodiments of the invention can be made without departing from the spirit and scope of the invention, the invention resides in the claims hereinafter appended.

We claim:

1. An advanced patient management system, comprising:
   an implantable medical device configured to generate a plurality of intra-cardiac electrograms and a plurality of event markers; and
   an external device including a repeater unit configured to collect the plurality of intra-cardiac electrograms and the plurality of event markers from the implantable medical device, the external device configured to:
      compile the plurality of intra-cardiac electrograms and the plurality of event markers over time as waveform data;
      categorize morphological aspects of the plurality of intra-cardiac electrograms into groups each representing a type of event marker of the plurality of event markers; and
      compare the morphological aspects of the plurality of intra-cardiac electrograms within at least one of the groups to identify changes in the morphological aspects of the plurality of intra-cardiac electrograms over time.

2. The system of claim 1, wherein the electrograms are generated using a plurality of intra-cardiac leads.

3. The system of claim 1, wherein the event markers represent events associated with leads of the implantable medical device.

4. The system of claim 1, wherein the waveform data includes a combination of electrograms having the same event markers at a given point in time.

5. The system of claim 1, wherein the repeater is configured to compile the plurality of electrograms.

6. The system of claim 1, wherein the external device further comprises a host in communication with the repeater through a network, wherein the host is configured to compile the plurality of electrograms.

7. A method of analyzing signal morphology in a patient using an implanted device, the method comprising:
   generating a plurality of electric signals and event markers with the implanted device;
   collecting the electric signals and event markers;
   compiling the collected electric signals and event markers as waveform data;
   categorizing morphological aspects of the collected electrical signals into groups each representing a type of event marker of the collected event markers; and
   detecting changes in morphological aspects of the collected electric signals over time by comparing the morphological aspects of the collected electrical signals within at least one of the groups using an external device configured to interrogate the implanted device.

8. The method of claim 7, further comprising communicating information about the collected electric signals and event markers to physician for analysis.

9. The method of claim 7, wherein collecting the electric signals and event markers includes collecting the electric signals and event markers using a repeater and communicating information about the collected electric signals and event markers to a host unit in communication with the repeater through a network, and wherein detecting the changes including detecting the changes automatically by the repeater or the host.

10. The method of claim 7, wherein compiling the collected electric signals and event markers includes aligning segments of at least two of the electric signals that represent a given beat of a patient's heart and that share a selected event marker.

11. The method of claim 7, wherein detecting the changes includes comparing the current waveform data to a predetermined waveform data.

12. The method of claim 7, wherein event markers include at least one of a atrial sense marker, a left ventricular sense marker, a right ventricular sense marker, an atrial pace marker, a left ventricular pace marker, and a right ventricular pace marker.

13. The method of claim 7, wherein detecting the changes includes extracting comparable waveform data.

14. The method of claim 13, wherein extracting comparable waveform data includes extracting waveform data specific to a lead of a pulse generator.

15. The method of claim 7, wherein compiling the collected electric signals and event markers as current waveform data includes binning the waveform data.

16. The method of claim 15, wherein binning the waveform data includes binning the waveform data based on maximum tracking rate (MTR) versus paced events at a lower rate limit (LRL).

17. The method of claim 15, wherein binning the waveform data includes binning the waveform data based on altered pacing support states comprising post-shock pacing or atrial tachycardia response mode switching.

18. The method of claim 7, further comprising using short and long term waveform data deviations to detect system faults.

19. The method of claim 7, wherein detecting the changes in waveform data includes using algorithms to detect the changes, the algorithms selected from higher order linear algorithms, non-linear algorithms, hysteretic algorithms, and adaptive threshold algorithms.

20. The method of claim 7, further comprising graphically presenting waveform data deviations for analysis by a medical technician.

* * * * *